United States Patent [19]

Lee et al.

[11] 4,430,260

[45] Feb. 7, 1984

[54] PENICILLIN-POLYVINYL ALCOHOL CONJUGATE AND PROCESS OF PREPARATION

[76] Inventors: Weng Y. Lee, 95 Rochester Pl.; Alec Sehon, 695 Academy Rd., both of Manitoba, Canada, R3N OE8

[21] Appl. No.: 312,890

[22] Filed: Oct. 19, 1981

Related U.S. Application Data

[62] Division of Ser. No. 15,864, Feb. 27, 1979, Pat. No. 4,296,097.

[51] Int. Cl.³ .................. C07D 499/00; A61K 31/43; A61K 39/385
[52] U.S. Cl. .................................. 260/239.1; 424/9; 424/78; 424/271
[58] Field of Search .................. 424/9, 78, 80, 271; 260/239.1

[56] References Cited

U.S. PATENT DOCUMENTS

| | | | |
|---|---|---|---|
| 2,155,658 | 4/1939 | Herrmann | 424/78 |
| 3,619,371 | 11/1971 | Crook | 424/88 X |
| 4,261,978 | 4/1981 | Lee | 424/78 |
| 4,296,097 | 10/1981 | Lee | 424/78 |

FOREIGN PATENT DOCUMENTS

| | | | |
|---|---|---|---|
| 880046 | 4/1953 | Fed. Rep. of Germany | 424/78 |
| 1135966 | 12/1968 | United Kingdom | 424/78 |

OTHER PUBLICATIONS

Sehon, J. Allergy Clin. Immunol., vol. 61, Mar. 1978, p. 179, Ab. No. 167.
Chiorazzi, Fed. Proc., vol. 35, 1976, Ab. No. 1258.
Chiller, Fed. Proc., vol. 35, 1976, Ab. No. 1259.
Pah, Fed. Proc. vol. 35, 1976 Ab. No. 1255.

*Primary Examiner*—Anne P. Fagelson
*Attorney, Agent, or Firm*—Fred Philpitt

[57] ABSTRACT

This invention relates to tolerogenic conjugates, suitable for use in suppressing the formation of reaginic antibodies in a host, of haptenic determinants, in particular the benzylpenicilloyl (BPO) group and 2,4-dinitrophenyl (DNP) group, with water-soluble, nonimmunogenic polymers, i.e. polyvinyl alcohols (PVA). The invention also comprises a method for the preparation of the conjugate and a method of suppressing the formation of these antibodies in a mammal sensitive to penicillin.

7 Claims, 3 Drawing Figures

PENICILLIN-POLYVINYL ALCOHOL CONJUGATE AND PROCESS OF PREPARATION

This is a division of application Ser No. 15,864, filed Feb. 27, 1979, now U.S. Pat. No. 4,296,097 and the benefits of 35 USC 120 are claimed relative to it.

The present invention relates to a conjugate for use for the suppression of reaginic antibodies in a person allergic to penicillin and to a method for making the conjugate.

One to 5% of the population in developed countries are allergic to penicillin. When penicillin is administered, they may go into anaphylactic shock or develop rashes or various other symptoms of penicillin hypersensitivity. The various allergic reactions to penicillin are mediated by different types of antibodies, the reactions of the "immediate type" being due to reaginic antibodies known as IgE antibodies. The benzylpenicilloyl (BPO) group has been shown to be the major immunogenic determinant in penicillin hypersensitivity.

The formation of anti-BPO IgE antibodies is primarily triggered by the haptenic BPO group. As any other hapten, BPO by itself does not induce the formation of IgE, but does so when conjugated with either (i) macromolecular contaminants or additives present in the penicillin preparation, or (ii) with the patient's own proteins or tissue components. The BPO conjugate(s) stimulates in the body appropriate lymphoid cells to produce anti-BPO IgE antibodies. These antibodies become attached to mast cells and basophils. Upon subsequent administration of penicillin, the polyvalent BPO conjugates (present in the penicillin preparation or formed by reaction with the patient's proteins) become attached to the anti-BPO IgE antibodies fixed to the mast cells or basophils. This antibody-antigen interaction results in bridging (i.e. crosslinking) of the cell fixed anti-BPO IgE antibodies and appears to be the prerequisite step for inducing the release from these cells of the granules containing histamine and other pharmacologically vasoactive compounds, which react with appropriate target organs leading thus to the inflammatory reactions underlying allergic manifestations.

Various methods have been used for the treatment of such allergic reactions; one pharmacological method involves the administration of antihistamines. Another method, based on immunochemical principles, involves the administration of a univalent BPO derivative, i.e. benzylpenicilloyl-formyl lysine (BPO-FLYS), which was synthesized by A. L. de Weck of Bern, Switzerland, and which is incapable of coupling to the host's constituents to form polyvalent allergens.* Such derivatives can attach themselves to each of the antigen binding sites of the individual IgE antibodies fixed to the mast cells or basophils, thereby blocking (preventing) the antigen binding sites of these antibodies for subsequent attachment to polyvalent molecules, i.e. thus, the possibility of triggering the release of granules from the cells is prevented. However, neither of these treatments prevents the formation of more IgE antibodies upon further exposure to the allergen.

*NOTE: This method is described in a paper entitled "Inhibition of Allergic Rections by Monovalent Haptens" by A. L. de Weck et al., which is published in the monograph "Mechanisms in Allergy. Reagin-Mediated Hypersensitivity", edited by L. Goodfriend, A. H. Sehon and R. P. Orange, p. 323, 1973, Marcel Dekker, Inc., N.Y.

In the novel method described here by the inventors, it was discovered that it is possible to suppress the formation of anti-BPO IgE reaginic antibodies by a judicious choice of a conjugate of BPO with a nonimmunogenic carrier, consisting of polyvinyl alcohols (PVA). Thus, treatment of either normal animals or of animals sensitized to BPO with a compound consisting of BPO attached to PVA was shown to induce immunological tolerance.

Immunological tolerance may be defined as a specific inhibition of the immune response to a given antigen. Thus, under certain conditions, the organism, instead of developing an immune response on exposure to a given antigen, may exhibit a state of immunological paralysis to the antigen in question, i.e. the administration of the particular antigen does not induce an immune response. However, the immune response of the host to other unrelated antigens remains normal. This state of immunologically specific tolerance is also known as immune paralysis and the substance capable of inducing tolerance, rather than antibody production, is referred to as a tolerogen. Clearly, the term tolerogenic is not synonymous with nonimmunogenic; the latter term indicates simply that a given compound is immunologically inert, i.e. it plays a passive role in relation to an immune response and is, therefore, not capable of triggering an immune response. By contrast, the term tolerogenic implies an active role for the corresponding antigen in suppressing, i.e. in shutting off, the immune response with respect to itself and related compounds.

In a paper published in the Journal of Immunology, Vol. 117, No. 3, Sept. 1976, pp. 927–934, the present inventors reported a regimen for the suppression of the formation of antibodies of the IgE class to the BPO group in experimental mice by administration of conjugates of BPO with the nonimmunogenic carrier, consisting of isologous γ-globulins, i.e. γ-globulins of murine origin. Similarly, the use of a synthetic polypeptide, i.e. the copolymer of D-glutamic acid and D-lysine (D-GL) as a carrier for BPO groups for the suppression of anti-BPO IgE response was also successful, as reported by Chiorazzi et al. (Chiorazzi, N., Eshhar, Z. and Katz, D. H., Proc. Nat. Acad. Sci. USA, 73:2091 [1976]). As described in the present submission, the inventors have discovered a new and more effective tolerogenic conjugate, which was prepared by coupling BPO to PVA. The resulting BPO-PVA conjugates were shown to suppress the anti-BPO IgE response in either normal or sensitized mice. In a parallel study, it was also shown that IgE antibodies directed against the 2,4-dinitrophenyl (DNP) group were also suppressed on administration of DNP-PVA conjugates. Accordingly, the present invention comprises conjugates suitable for suppressing the formation of reaginic antibodies in a host to small haptenic groups, e.g. BPO and DNP, by injection of the conjugates of these groups with the nonimmunogenic, water-soluble polymer, namely PVA.

In the particular case of the tolerogenic conjugates prepared in this study, these conjugates contained an average of 0.7–3.9 BPO or DNP groups per molecule of PVA of molecular weight in the range of 10,000–14,000.

This invention comprises also a process for activating PVA with cyanogen bromide, followed by reaction with 1,6-hexane diamine so as to graft amino groups onto the PVA molecules. Penicillin was then reacted with the amino derivatives of PVA at alkaline pH.

In addition, the invention comprises a process for the suppression of the formation of anti-BPO reaginic antibodies in a mammal sensitive to penicillin by injecting the conjugate into the sensitized individual in a pharmaceutically acceptable manner.

The preferred nonimmunogenic, tolerogenic carriers are polyvinyl alcohols of molecular weights of 10,000 and 14,000.

The reaction of penicillin with the amino derivative of PVA is carried out in the presence of a suitable salt which permits the reaction to proceed at a pH of about 9.8. Suitable salts include potassium carbonate and sodium carbonate.

The present invention will be illustrated in the following nonlimiting Examples and Tables.

MATERIALS AND METHODS

Animals

Inbred 8- to 12-week old ($C_{57}BL/6 \times DBA/2)F_1$ mice (designated as $B_6D_2F_1$) were purchased from Jackson Laboratories, Bar Harbor, Maine. For the passive cutaneous anaphylaxis (PCA) assays, random-bred hooded rats, supplied by Bio-Breeding Laboratories Ltd., Ottawa, were used.

Preparation of amino derivative of PVA (PVA-$NH_2$)

For the sake of brevity, PVA of molecular weights of 10,000 and 14,000 will be referred to hereafter as $PVA_{10}$ and $PVA_{14}$, respectively. To $PVA_{10}$ or $PVA_{14}$ (10 gm) dissolved in 200 ml of distilled water was added 5 gm by cyanogen bromide. The pH of the reaction mixture was maintained at 11 by dropwise addition of 2 N NaOH. Twenty minutes later, 10 gm of 1,6-hexane diamine was added to the mixture and stirred for 48 hours at room temperature. The reaction mixture was then dialyzed exhaustively against distilled water and lyophilized.

Preparation of BPO-PVA

PVA-$NH_2$ (400 mg) was dissolved in 20 ml distilled water. After addition of 400 mg of penicillin G (potassium salt, Pfizer Company Ltd., Montreal) and 4 ml of 1 M $K_2CO_3$, the mixture was stirred for 2½ hours at room temperature. The unreacted penicillin G was removed by gel filtration on Sephadex G-25 column. The sample was dialyzed and lyophilized. The degree of substitution, i.e. the number of BPO groups coupled per PVA molecule, was determined by quantitative titration with mercuric chloride solution according to the method of Parker et al. (Journal of Experimental Medicine, Vol. 115, p. 803, 1962) and found to be 2.8. The other $BPO_x$-PVA conjugates of varying epitope density prepared in this study, i.e. $PBO_{0.7}$-$PVA_{10}$, $BPO_{1.1}$-$PVA_{10}$, $BPO_2$-$PVA_{10}$, $BPO_{2.7}$-$PVA_{10}$, $BPO_{2.8}$-$PVA_{10}$, $BPO_{2.7}$-$PVA_{14}$ and $BPO_{3.9}$-$PVA_{14}$, were prepared in a similar fashion by adjusting appropriately the concentration of penicillin G and allowing the reaction to proceed for different times.

Preparation of DNP-PVA

To a solution of 50 ml of 0.4 M $Na_2CO_3$ containing 0.5 gm of PVA-$NH_2$ was added 0.5 gm of sodium 2,4-dinitrobenzene sulfonate (Baker Chemical Co., Phillipsburg, N.Y.) and the mixture was incubated at 37° C. for 3 days. The precipitate, which formed during the incubation period, was removed by centrifugation at 18,000 rpm in a Sorvall RC2-B centrifuge for 20 min. The supernatant was passed through a column (4×60 cm) of Sephadex G-25 gel to eliminate any unreacted hapten. The effluent containing the conjugate was dialyzed against distilled water and lyophilized. The degree of substitution of DNP groups, i.e. the average number of DNP groups grafted onto a PVA molecule, was determined spectrophotometrically taking the molar absorption coefficient for DNP as 17,400 at 360 nm, and was found to be 1.5.

The precipitate collected by centrifugation as described above was dissolved in distilled water, dialyzed exhaustively and lyophilized. The degree of substitution of this sample was found to be 2.4.

The conjugate $DNP_{3.1}$-$PVA_{10}$ was similarly prepared except that the $Na_2CO_3$ concentration was lowered to 0.2 M and the reaction mixture was stirred for 2 days at room temperature. The conjugate $DNP_{4.3}$-$PVA_{14}$ was prepared as $DNP_{3.1}$-$PVA_{10}$ with the exception that 0.75 gm of $PVA_{14}$-$NH_2$ was used in the reaction mixture.

Preparation of hapten-protein conjugates

The benzylpenicilloyl-ovalbumin ($BPO_4$-OA) and benzylpenicilloyl-bovine γ-globulin ($BPO_{17}$-BGG) conjugates were prepared as described in a previous study (Lee, W. Y. and Sehon, A. H., J. Immunol. 117:927 [1976]) and the $DNP_3$-OA and $DNP_{18}$-BGG conjugates were synthesized as reported earlier (Lee, W. Y. and Sehon, A. H., J. Immunol. 114:829 [1975]). The 2,4-dinitrophenylated extract of *Ascaris suum* (DNP-ASC), which contained $6.5 \times 10^{-8}$ M DNP per mg of ASC, was prepared by reacting 46 mg of ASC with 24 mg of DNBS in the presence of 46 mg of $Na_2CO_3$ in a total volume of 5.5 ml of distilled water at 37° C. for 2 hours.

Immunization and measurement of reaginic antibody responses

For the optimal elicitation of anti-DNP and anti-OA IgE responses, mice were injected i.p. with the standard, low dose of 1 μg of $DNP_3$-OA suspended with 1 mg of freshly prepared aluminum hydroxide in 0.5 ml of phosphate buffered saline (PBS). This dose, when administered by the i.p. route, will be referred to hereafter as the sensitizing dose of $DNP_3$-OA.

The optimal anti-BPO IgE response was induced in mice by i.p. injection of 10 μg of $BPO_4$-OA in presence of 1 mg of $Al(OH)_3$. Mice were also sensitized with 10 μg of DNP-ASC premixed with 1 mg of $Al(OH)_3$ in 0.5 ml of PBS for the induction of anti-DNP and anti-ASC IgE antibodies. Groups of four to five mice were treated in an identical manner and the sera of mice within each group were pooled for determination of the average reaginic titer by the passive cutaneous anaphylaxis (PCA) assay. The end point of the titration was taken as the reciprocal of the highest dilution of each serum resulting in a reaction of 5 mm in diameter. The PCA titers are reported as averages of two determinations.

Adoptive cell transfer

This procedure consisted of the transfer of spleen cells from sensitized and/or tolerized mice into X-irradiated (650 R) syngeneic recipients and injection of the recipients with the standard sensitizing dose of antigen in presence of $Al(OH)_3$ within 4 hours after cell transfer.

EXAMPLE 1: SUPPRESSION OF IgE RESPONSE SPECIFIC FOR BENZYLPENICILLOYL GROUP

(A) Suppression of the Induction of Anti-BPO IgE Response with $BPO_2$-$PVA_{10}$ or $BPO_{2.7}$-$PVA_{14}$ Mice were injected i.p with $BPO_2$-$PVA_{10}$ or $BPO_{2.7}$-$PVA_{14}$, in doses of 0.5 or 1.0 mg per recipient, 7 days prior to sensitization with $BPO_4$-OA in presence of $Al(OH)_3$. The primary IgE responses were determined 14 days after sensitization. For the induction of the secondary and tertiary IgE responses, all mice were reimmunized with sensitizing doses of $BPO_4$-OA on days 28 and 56, respectively, and the PCA titers were determined 7 days after sensitization. The results indicated in Table I clearly show that the anti-BPO IgE response was profoundly suppressed in spite of repeated challenge of these animals with the sensitizing dose of the antigen without, however, affecting appreciably the anti-OA IgE response.

(B) Suppression of the Anti-BPO IgE Response in Sensitized Animals with $BPO_2$-$PVA_{10}$ The ability of $BPO_2$-$PVA_{10}$ to abrogate an ongoing anti-BPO IgE response was tested in sensitized animals as illustrated in Table II. All mice received sensitizing doses of $BPO_4$-OA on days 0, 28 and 56. Mice in test groups received additional injections of 0.5, 0.75 or 1.0 mg of $BPO_2$-$PVA_{10}$ 21 days after primary sensitization of mice. As is evident from the PCA results determined with sera obtained on day 35, which are listed in Table II, the ongoing anti-BPO IgE response was completely abolished after injection of the tolerogen 7 days before the secondary sensitization. Moreover, as supported by the PCA titers of sera of mice which received a third sensitizing dose of $BPO_4$-OA, these mice had remained immunosuppressed for at least 36 days after receiving an injection of the tolerogenic $BPO_2$-$PVA_{10}$ preparation.

(C) Effect of Dose of $BPO_{2.7}$-$PVA_{14}$ on the Abrogation of the Anti-BPO Response in Sensitized Mice Various doses ranging from 0.1 to 1.0 mg of $BPO_{2.7}$-$PVA_{14}$ were injected into mice which had been sensitized 21 days earlier. As indicated in Table III, a single dose of 0.25 mg of $BPO_{2.7}$-$PVA_{14}$ was sufficient to abolish completely an ongoing anti-BPO IgE response.

(D) Tolerogenicity of $BPO_x$-$PVA_{10}$ Conjugates with Different Epitope Density in Sensitized Mice The effect of different epitope density (i.e. degree of substitution) on the tolerogenicity of conjugates of BPO with PVA was studied by injecting 1 mg of these conjugates i.p. into mice which had been sensitized with $BPO_4$-OA suspended in $Al(OH)_3$ 21 days earlier. One week after injection of the tolerogen, all mice were immunized with a sensitizing dose of $BPO_4$-OA and the PCA titers were determined 7 days later. The results shown in Table IV demonstrate that complete suppression of anti-BPO IgE response was achieved by injection of 1 mg of $BPO_x$-$PVA_{10}$ conjugate with an epitope density in excess of 1.1 and that conjugates of lower epitope density, e.g. $BPO_{0.7}$-$PVA_{10}$, suppressed only partially the anti-BPO IgE response. It is to be stressed that the suppression of anti-BPO IgE response was antigen specific, since the accompanying anti-OA IgE response was not affected.

EXAMPLE 2: SUPPRESSION OF IgE RESPONSE SPECIFIC FOR DNP GROUP

(A) Suppression of Anti-DNP IgE Response with $DNP_{3.4}$-$PVA_{10}$

Figure 1:
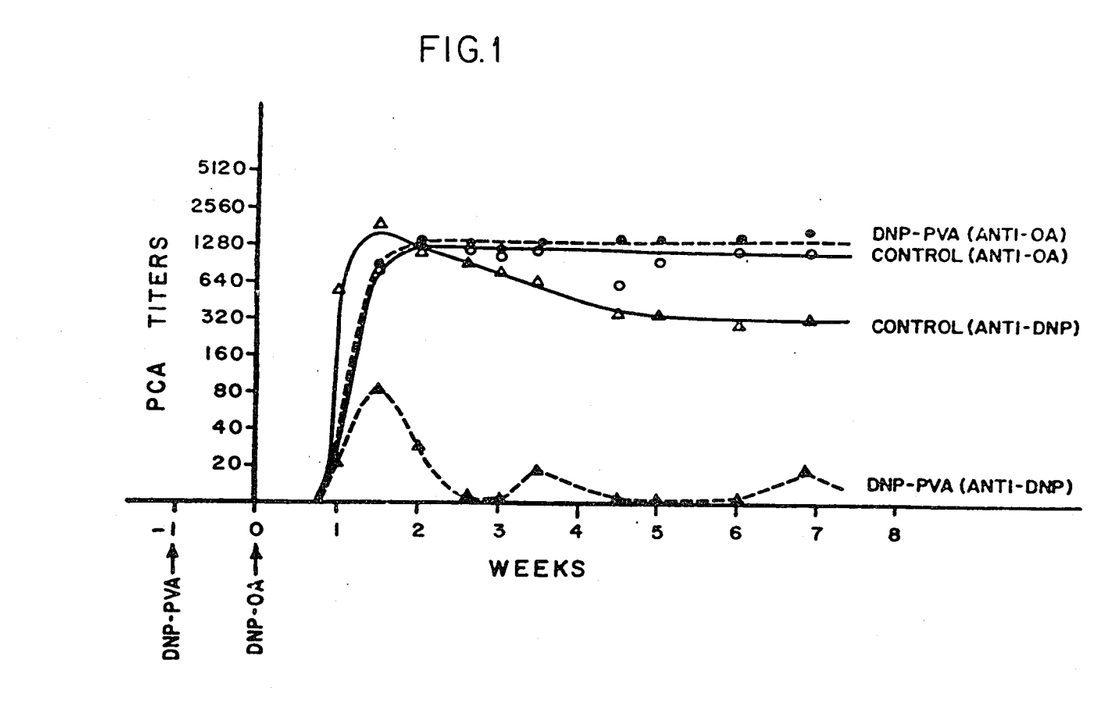
FIG. 1.—Suppression of the induction of anti-DNP IgE response

The suppression of the induction of anti-DNP IgE response was studied by injecting a single dose of 1 mg of $DNP_{3.4}$-$PVA_{10}$ into normal mice one week prior to sensitization with the standard dose of 1 μg of $DNP_3$-OA in presence of 1 mg of $Al(OH)_3$. The results plotted in FIG. 1 show that the anti-DNP IgE response was profoundly suppressed in mice treated with this conjugate. The suppression was antigen specific as demonstrated by the fact that the anti-OA IgE response was virtually unaffected.

Figure 2:
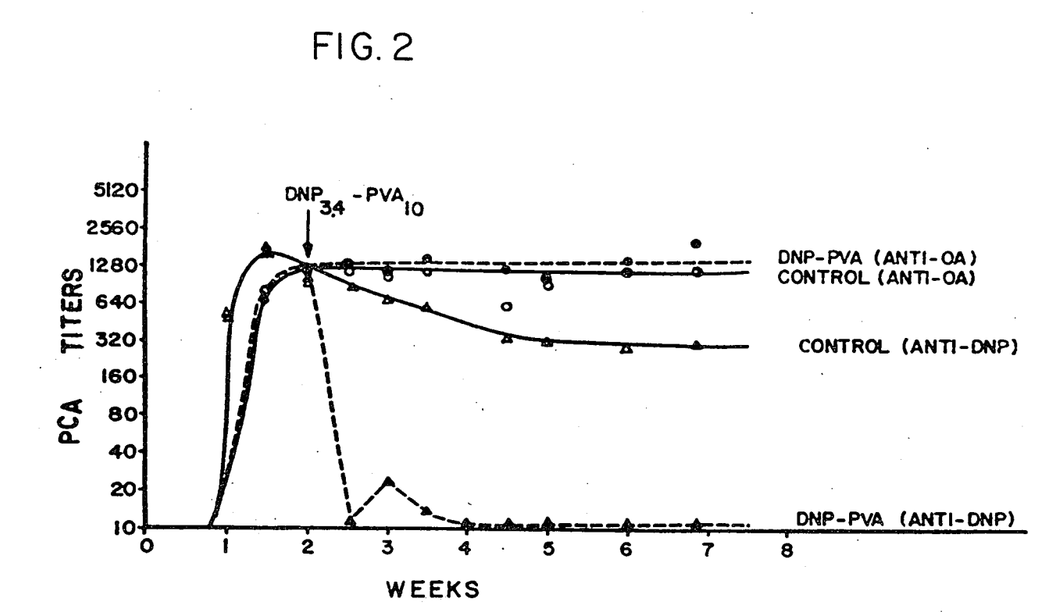

(B) Abrogation of an Ongoing Anti-DNP IgE Response with $DNP_{3.4}$-$PVA_{10}$ The possibility of using the above immunosuppressive approach for the abrogation of an ongoing anti-DNP IgE response was explored by injection of 1 mg of $DNP_{3.4}$-$PVA_{10}$ into mice which had been sensitized with $DNP_3$-OA 14 days earlier as shown in FIG. 2. It is clear that the anti-DNP IgE response was abrogated readily after injection of the tolerogen. However, these mice produced high level of IgE response to OA which was indistinguishable from those produced by the control mice.

(C) Effect of Dose of $DNP_{4.3}$-$PVA_{14}$ on Suppression of Anti-DNP IgE Response Mice were injected i.p. with varying doses of the tolerogen 7 days prior to sensitization with $DNP_3$-OA in presence of $Al(OH)_3$. From the results listed in Table V, it is evident that a significant degree of suppression of the anti-DNP IgE response was achieved with all the doses tested and that the higher doses were more effective in inducing immunosuppresion. Upon challenge with a secondary sensitizing dose of $DNP_3$-OA on day 28, the mice which had received the tolerogen exhibited almost total immunosuppression or their anti-DNP IgE response remained markedly dampened.

(D) Effect of time of Injection of $DNP_{4.3}$-$PVA_{14}$ on Reaginic Antibody Formation Mice were injected i.p. with the tolerogen (1 mg per mouse) on various days before or after immunization with DNP-OA in $Al(OH)_3$. Sera were collected at the peak of reaginic antibody response and assayed for PCA activities as indicated in Table VI. It is obvious that the anti-DNP IgE response could be readily suppressed regardless of the time of injection. Moreover, the immunosuppression was more profound when the tolerogen was injected close to time of immunization, i.e. from day −7 to day 4.

(E) Abrogation of Anti-DNP IgE Response with $DNP_{2.4}$-$PVA_{10}$ in Sensitized Mice For the abrogation of an ongoing anti-DNP IgE response, mice which had been sensitized with $DNP_3$-OA 59 days earlier were injected with 1 mg of $DNP_{2.4}$-$PVA_{10}$ and resensitized on the following day. As is evident from Table VII, the anti-DNP response was suppressed significantly. To test the duration of the unresponsive state, these mice received two additional sensitizing doses of $DNP_3$-OA at 4-week intervals. It is obvious from Table VII that the unresponsive state was long lasting despite the administration of repeated sensitizing injections of DNP$_3$-OA.

(F) Specificity of Immunosuppression by DNP$_{2.4}$-PVA$_{10}$

It has been shown in previous sections that injection of mice with DNP-PVA conjugates suppressed specifically the anti-DNP response. Hence, this experiment was designed to examine the effect of DNP-PVA on the anti-DNP IgE response induced by DNP conjugates with different carriers. For this purpose, mice were injected with 1 mg of DNP$_{2.4}$-PVA$_{10}$ two days before sensitization with a standard dose of DNP$_3$-OA (Expt. 1) or DNP-ASC (Expt. 2), followed by resensitization 4 weeks later with a DNP conjugate with different carrier, namely DNP-ASC (Expt. 1) or DNP-OA (Expt. 2), as indicated in Table VIII. The results demonstrated that the anti-DNP IgE response was effectively suppressed regardless of the nature of the carrier used for sensitization.

(C) Active Suppression of Anti-DNP IgE Response of Primed Cells with Tolerized Cells in Adoptive Transfer System In order to study the possibility of induction of suppressor cells by the treatment with DNP-PVA, the adoptive cell transfer system was used. Different combinations of spleen cells from primed and tolerized mice were transferred into X-irradiated (650 R) recipients. The primed donors were sensitized with DNP$_3$-OA 30 days before the cell transfer; the tolerized donors received an additional injection of 1 mg of DNP$_{2.4}$-PVA$_{10}$ 7 days prior to cell transfer. The results illustrated in FIG. 3 clearly show that the tolerized cells remained unresponsive in the X-irradiated recipients. Moreover, these tolerized cells suppressed actively the anti-DNP IgE response of primed cells in the cell mixture. This finding indicates that DNP-specific suppressor cells are present in the tolerized cell populations.

(H) Maintenance of Unresponsiveness in Adoptive Cell Transfer System

The donor mice were presensitized with a sensitizing dose of DNP$_3$-OA 49 days before the cell transfer. As indicated in Table IX, at various times prior to cell transfer, the donors received an additional i.p. injection of 1 mg of DNP$_{2.4}$-PVA$_{10}$. The spleen cells of these donors ($3 \times 10^7$) were transferred into X-irradiated (650 R) recipients which received a sensitizing dose of DNP$_3$-OA within 4 hours after cell transfer. The results shown in Table IX demonstrate that the spleen cells from donors tolerized 5 hours or 1 day prior to transfer did not show significant suppression in the X-irradiated recipients. On the other hand, the spleen cells of donors which had received DNP$_{2.4}$-PVA$_{10}$ 2 days to 14 days prior to cell transfer remained unresponsive in the X-irradiated recipients. This implies that treatment of mice with DNP$_{2.4}$-PVA$_{10}$ requires at least 2 days to render the cells unresponsive.

(I) Prevention of Systemic Anaphylaxis by Treatment of Sensitized Mice with DNP$_{2.4}$-PVA$_{10}$ Since it has been shown in previous sections that an ongoing anti-DNP IgE response could be readily abrogated by treatment of sensitized mice with DNP-PVA conjugates, the present experiment was designed to examine if systemic reactions could occur in these immunosuppressed animals when they were challenged i.v. with a multivalent DNP-protein conjugate (i.e. DNP$_9$-M$\gamma$G) or OA. In order to render the mice sensitive for the demonstration of systemic anaphylaxis, the administration of B. pertussis in addition to the sensitizing antigen was found to be essential. As indicated in Table X, treatment of mice with 1 mg of DNP$_{2.4}$-PVA$_{10}$ suppressed completely the anti-DNP IgE response, whereas the anti-carrier IgE response was not affected. More importantly, whereas the control sensitized mice died of anaphylaxis after i.v. challenge of DNP$_9$-M$\gamma$G, the mice rendered tolerant by this treatment did not show any discomfort on i.v. challenge with DNP$_9$-M$\gamma$G. Moreover, i.v. challenge with OA led to the death of both groups of mice indicating, thus, that the immunosuppression was highly antigen specific.

TABLE I

| | PCA TITERS | | | | | |
|---|---|---|---|---|---|---|
| | PRIMARY | | SECONDARY | | TERTIARY | |
| TOLEROGEN INJECTED* | ANTI-BPO | ANTI-OA | ANTI-BPO | ANTI-OA | ANTI-BPO | ANTI-OA |
| BPO$_2$—PVA$_{10}$, 0.5 mg | <10 | 1,450 | 20 | 3,160 | 1,260 | 5,370 |
| BPO$_2$—PVA$_{10}$, 1.0 mg | <10 | 1,580 | <10 | 2,820 | 360 | 4,360 |
| BPO$_{2.7}$—PVA$_{14}$, 0.5 mg | <10 | 1,740 | 10 | 3,980 | 360 | 6,030 |
| BPO$_{2.7}$—PVA$_{14}$, 1.0 mg | <10 | 680 | <10 | 3,020 | 320 | 5,620 |
| CONTROL MICE | 30 | 1,910 | 810 | 3,980 | 2,750 | 6,920 |

SUPPRESSION OF THE INDUCTION OF ANTI-BPO IgE RESPONSE WITH BPO$_2$—PVA$_{10}$ OR BPO$_{2.7}$—PVA$_{14}$

*Mice were injected i.p. with BPO$_2$—PVA$_{10}$ or BPO$_{2.7}$—PVA$_{14}$ 7 days prior to sensitization with BPO$_4$—OA in presence of Al(OH)$_3$. The primary IgE responses were determined 14 days after sensitization. For the induction of secondary and tertiary IgE responses, all mice were immunized with sensitizing doses of BPO$_4$—OA on days 28 and 56, respectively, and the PCA titers were determined 7 days after sensitization.

TABLE II

ABROGATION OF ANTI-BPO IgE RESPONSE WITH BPO$_2$—PVA$_{10}$ IN SENSITIZED ANIMALS

| | TREATMENT* | | PCA TITERS | |
|---|---|---|---|---|
| GROUP | DAY | COMPOUND | DAY | ANTI-BPO | ANTI-OA |
| CONTROL | 0 | BPO$_4$—OA | 14 | 90 | 3,100 |
| | 28 | BPO$_4$—OA | 35 | 870 | 3,630 |
| | 56 | BPO$_4$—OA | 63 | 1,450 | 4,170 |
| TEST 1 | 0 | BPO$_4$—OA | 14 | 90 | 3,100 |
| | 21 | BPO$_2$—PVA$_{10}$, 0.5 mg | | | |
| | 28 | BPO$_4$—OA | 35 | <10 | 5,370 |
| | 56 | BPO$_4$—OA | 63 | 930 | 6,920 |
| TEST 2 | 0 | BPO$_4$—OA | 14 | 90 | 3,100 |
| | 21 | BPO$_2$—PVA$_{10}$, 0.75 mg | | | |
| | | BPO$_4$—OA | 35 | <10 | 3,240 |
| | 56 | BPO$_4$—OA | 63 | <10 | 5,370 |
| TEST 3 | 0 | BPO$_4$—OA | 14 | 90 | 3,100 |
| | 21 | BPO$_2$—PVA$_{10}$, 1.0 mg | | | |
| | 28 | BPO$_4$—OA | 35 | <10 | 4,470 |

TABLE II-continued

ABROGATION OF ANTI-BPO IgE RESPONSE WITH BPO$_2$—PVA$_{10}$ IN SENSITIZED ANIMALS

| | TREATMENT* | | PCA TITERS | |
|---|---|---|---|---|
| GROUP | DAY | COMPOUND | DAY | ANTI-BPO | ANTI-OA |
| | 56 | BPO$_4$—OA | 63 | 360 | 6,610 |

*All mice received sensitizing doses of BPO$_4$—OA on days 0, 28 and 56. Mice in the test groups received additional injections of 0.5 mg (TEST 1), 0.75 mg (TEST 2) or 1.0 mg (TEST 3) of BPO$_2$—PVA$_{10}$ on day 21.

TABLE III

EFFECT OF DOSE OF BPO$_{2.7}$—PVA$_{14}$ ON THE ABROGATION OF ANTI-BPO RESPONSE IN SENSTIZED MICE

| | TREATMENT* | | | PCA TITERS | |
|---|---|---|---|---|---|
| GROUP | DAY | COMPOUND | DAY | ANTI-BPO | ANTI-OA |
| CONTROL | 0 | BPO$_4$—OA | 14 | 70 | 4,000 |
| | 28 | BPO$_4$—OA | 35 | 1,050 | 4,570 |
| | 56 | BPO$_4$—OA | 63 | 1,350 | 3,630 |
| TEST 1 | 0 | BPO$_4$—OA | 14 | 70 | 4,000 |
| | 21 | BPO$_{2.7}$—PVA$_{14}$, 0.1 mg | | | |
| | 28 | BPO$_4$—OA | 35 | 20 | 5,750 |
| | 56 | BPO$_4$—OA | 63 | 790 | 4,470 |
| TEST 2 | 0 | BPO$_4$—OA | 14 | 70 | 4,000 |
| | 21 | BPO$_{2.7}$—PVA$_{14}$, 0.25 mg | | | |
| | 28 | BPO$_4$—OA | 35 | <10 | 3,800 |
| | 56 | BPO$_4$—OA | 63 | 100 | 3,380 |
| TEST 3 | 0 | BPO$_4$—OA | 14 | 70 | 4,000 |
| | 21 | BPO$_{2.7}$—PVA$_{14}$, 0.5 mg | | | |
| | 28 | BPO$_4$—OA | 35 | <10 | 5,370 |
| | 56 | BPO$_4$—OA | 63 | 90 | 2,950 |
| TEST 4 | 0 | BPO$_4$—OA | 14 | 70 | 4,000 |
| | 21 | BPO$_{2.7}$—PVA$_{14}$, 1.0 mg | | | |
| | 28 | BPO$_4$—OA | 35 | <10 | 5,750 |
| | 56 | BPO$_4$—OA | 63 | 100 | 2,560 |

*All mice received sensitizing doses of BPO$_4$—OA on days 0, 28 and 56. Mice in the test groups received additional injections of various doses of BPO$_{2.7}$—PVA$_{14}$ on day 21.

TABLE IV

TOLEROGENICITY OF BPO$_x$—PVA$_{10}$ CONJUGATES WITH DIFFERENT EPITOPE DENSITY IN SENSITIZED MICE

| | PCA TITERS | |
|---|---|---|
| TREATMENT* | ANTI-BPO | ANTI-OA |
| BPO$_{0.7}$—PVA$_{10}$ | 280 | 6,170 |
| BPO$_{1.1}$—PVA$_{10}$ | <10 | 3,800 |
| BPO$_{2.0}$—PVA$_{10}$ | <10 | 3,550 |
| BPO$_{2.7}$—PVA$_{10}$ | <10 | 5,750 |
| BPO$_{2.8}$—PVA$_{10}$ | <10 | 3,980 |
| BPO$_{3.9}$—PVA$_{14}$ | <10 | 5,120 |
| CONTROL MICE | 1,050 | 4,570 |

*All mice were presensitized with BPO$_4$—OA 21 days prior to i.p. injections of 1 mg of BPO$_x$—PVA$_{10}$ conjugates of different epitope density. One week after the injection of BPO$_x$—PVA$_{10}$, mice were sensitized with BPO$_4$—OA and the PCA titers determined 7 days later.

TABLE V

EFFECT OF DOSE OF DNP$_{4.3}$—PVA$_{14}$ ON SUPPRESSION OF ANTI-DNP IgE RESPONSES

| | PCA TITERS | | | |
|---|---|---|---|---|
| | PRIMARY | | SECONDARY | |
| DOSE OF TOLEROGEN* | ANTI-DNP | ANTI-OA | ANTI-DNP | ANTI-OA |
| 0.25 mg | 90 | 830 | 330 | 3,310 |
| 0.5 mg | 80 | 1,280 | 150 | 1,450 |
| 0.75 mg | 20 | 510 | 70 | 1,120 |
| 1.0 mg | 10 | 380 | 70 | 2,460 |
| 1.5 mg | 20 | 1,410 | 40 | 3,160 |
| 2.0 mg | <10 | 160 | 10 | 2,460 |
| CONTROL MICE | 380 | 500 | 870 | 1,180 |

*Mice were injected i.p. with varying doses of the tolerogen 7 days prior to sensitization with DNP$_3$—OA in presence of Al(OH)$_3$. The primary IgE responses were determined on day 14 after sensitization. All mice were sensitized again on day 28 for the secondary responses. The secondary anti-DNP and anti-OA IgE responses were measured 7 days after immunization.

TABLE VI

EFFECT OF TIME OF INJECTION OF DNP$_{4.3}$—PVA$_{14}$ ON REAGINIC ANTIBODY FORMATION

| | PCA TITERS | | | |
|---|---|---|---|---|
| | PRIMARY | | SECONDARY | |
| TIME OF TREATMENT* | ANTI-DNP | ANTI-OA | ANTI-DNP | ANTI-OA |
| Day −14 | 90 | 1,580 | 70 | 3,160 |
| DAY −10 | 210 | 1,580 | 220 | 3,800 |
| DAY −7 | 30 | 1,280 | 150 | 2,950 |
| DAY −3 | 30 | 1,320 | 30 | 2,400 |
| DAY −1 | 50 | 1,280 | 50 | 2,630 |
| DAY 0 | 30 | 1,280 | 20 | 4,170 |
| DAY 1 | 90 | 1,510 | 80 | 6,610 |
| DAY 4 | 70 | 1,380 | 90 | 3,980 |
| DAY 7 | 190 | 2,340 | 330 | 5,750 |
| DAY 14 | (1,050) | (1,320)** | 70 | 5,890 |
| DAY 21 | (1,050) | (1,320)** | 180 | 6,460 |
| CONTROL MICE | 1,050 | 1,320 | 1,510 | 3,090 |

*Animals were treated with the tolerogen on the same day (i.e. day 0), or before, or after i.p. immunization with DNP$_3$—OA in Al(OH)$_3$. The primary IgE responses were determined on day 14 after immunization. For the induction of secondary responses, all mice were sensitized with DNP$_3$—OA on day 28 and the PCA titers were determined 7 days later.

**These PCA titers represent the primary responses prior to the injection of tolerogen.

TABLE VII

ABROGATION OF ANTI-DNP IgE RESPONSE WITH $DNP_{2.4}$—$PVA_{10}$ IN SENSITIZED ANIMALS

| GROUP | TREATMENT* DAY | COMPOUND | PCA TITERS DAY | ANTI-DNP | ANTI-OA |
|---|---|---|---|---|---|
| CONTROL | 0 | $DNP_3$—OA | 7 | 3,020 | 7,940 |
|  |  |  | 14 | 3,320 | 3,800 |
|  | 28 | $DNP_3$—OA | 35 | 3,020 | 6,840 |
|  |  |  | 42 | 3,020 | 6,760 |
|  | 56 | $DNP_3$—OA | 63 | 3,020 | 5,750 |
|  |  |  | 70 | 2,280 | 4,820 |
| TEST | −1 | $DNP_{2.4}$—$PVA_{10}$, 1 mg |  |  |  |
|  | 0 | $DNP_3$—OA | 7 | 260 | 6,840 |
|  |  |  | 14 | 350 | 3,470 |
|  | 28 | $DNP_3$—OA | 35 | 230 | 9,120 |
|  |  |  | 42 | 260 | 6,760 |
|  | 56 | $DNP_3$—OA | 63 | 390 | 6,760 |
|  |  |  | 70 | 180 | 5,490 |

*All mice, which had been sensitized with 1 μg $DNP_3$—OA in the presence of 1 mg $Al(OH)_3$ 60 days before the experiment, received three sensitizing doses of $DNP_3$—OA on days 0, 28 and 56. Mice in test group received an additional i.p. injection of 1 mg $DNP_{2.4}$—$PVA_{10}$ on day −1.

TABLE VIII

SPECIFICITY OF IMMUNOSUPPRESSION BY $DNP_{2.4}$—$PVA_{10}$

| GROUP | TREATMENT* DAY | COMPOUND | PCA TITERS DAY | ANTI-DNP | ANTI-OA | ANTI-ASC |
|---|---|---|---|---|---|---|
| EXPERIMENT 1 |  |  |  |  |  |  |
| CONTROL | −2 | SALINE |  |  |  |  |
|  | 0 | $DNP_3$—OA | 7 | <10 | <10 | N.T.** |
|  |  |  | 14 | 1,700 | 1,820 | N.T. |
|  | 28 | DNP—ASC | 35 | 3,470 | 3,160 | 20 |
|  |  |  | 42 | 2,690 | 830 | 70 |
| TEST | −2 | $DNP_{2.4}$—$PVA_{10}$ |  |  |  |  |
|  | 0 | $DNP_3$—OA | 7 | <10 | <10 | N.T. |
|  |  |  | 14 | 20 | 1,740 | N.T. |
|  | 28 | DNP—ASC | 35 | <10 | 1,700 | 10 |
|  |  |  | 42 | <10 | 760 | 80 |
| EXPERIMENT 2 |  |  |  |  |  |  |
| CONTROL | −2 | SALINE |  |  |  |  |
|  | 0 | DNP—ASC | 7 | <10 | N.T. | <10 |
|  |  |  | 14 | 300 | N.T. | 100 |
|  | 28 | $DNP_3$—OA | 35 | 3,540 | 80 | 370 |
|  |  |  | 42 | 3,500 | 480 | 320 |
| TEST | −2 | $DNP_{2.4}$—$PVA_{10}$ |  |  |  |  |
|  | 0 | DNP—ASC | 7 | <10 | N.T. | <10 |
|  |  |  | 14 | <10 | N.T. | 80 |
|  | 28 | $DNP_3$—OA | 35 | <10 | 20 | 240 |
|  |  |  | 42 | 20 | 810 | 80 |

*In experiment 1, all mice received sensitizing doses of $DNP_3$—OA and DNP—ASC on days 0 and 28, respectively. The test mice received additional injections of 1 mg of $DNP_{2.4}$—$PVA_{10}$ on day −2.
In experiment 2, all mice were immunized with sensitizing doses of DNP—ASC and $DNP_3$—OA on days 0 and 28, respectively. The test mice were pretreated with 1 mg of $DNP_{2.4}$—$PVA_{10}$ on day −2.
**N.T. = not tested since the animals were not immunized with the corresponding carriers.

TABLE IX

TIME OF TREATMENT OF SENSITIZED CELL DONORS WITH $DNP_{2.4}$—$PVA_{10}$ PRIOR TO ADOPTIVE CELL TRANSFER

| TIME OF TREATMENT OF CELL DONORS PRIOR TO CELL TRANSFER* | PCA TITERS** | |
|---|---|---|
| | ANTI-DNP | ANTI-OA |
| 5 hours | 900 | 1,910 |
| 1 day | 920 | 1,950 |
| 2 days | 100 | 2,000 |
| 3 days | 300 | 1,910 |
| 4 days | 80 | 1,950 |
| 7 days | 80 | 1,900 |
| 14 days | 90 | 1,800 |
| CONTROL MICE | 1,430 | 2,400 |

*Donors of spleen cells were preimmunized with a sensitizing dose of $DNP_3$—OA on day −49. A single dose of 1 mg $DNP_{2.4}$—$PVA_{10}$ was injected i.p. into these donors at various times prior to transfer of their spleen cells ($3 \times 10^7$) into X-irradiated (650 R) recipients. These recipients were challenged within 4 hours with a sensitizing dose of $DNP_3$—OA.
**The PCA titers were assayed 14 days after cell transfer.

LEGENDS TO FIGURES

All mice received an i.p. sensitizing dose of 1 µg $DNP_3$-OA in presence of 1 mg $Al(OH)_3$. Mice in test group received an additional i.p. injection of 1 mg $DNP_{3.4}$-$PVA_{10}$ 7 days prior to sensitization. The IgE responses specific for the DNP determinant (Δ—Δ) and for the carrier (O—O) are expressed in terms of PCA titers.

FIG. 2.—Abrogation of an ongoing anti-DNP IgE response with $DNP_{3.4}$-$PVA_{10}$ All mice were sensitized with 1 µg $DNP_3$-OA in presence of 1 mg $Al(OH)_3$. Mice in the test group received an additional i.p. injection of 1 mg $DNP_{3.4}$-$PVA_{10}$ 14 days after sensitization. The IgE responses specific for the DNP determinant and the carrier are represented by triangles and circles, respectively.

Figure 3:
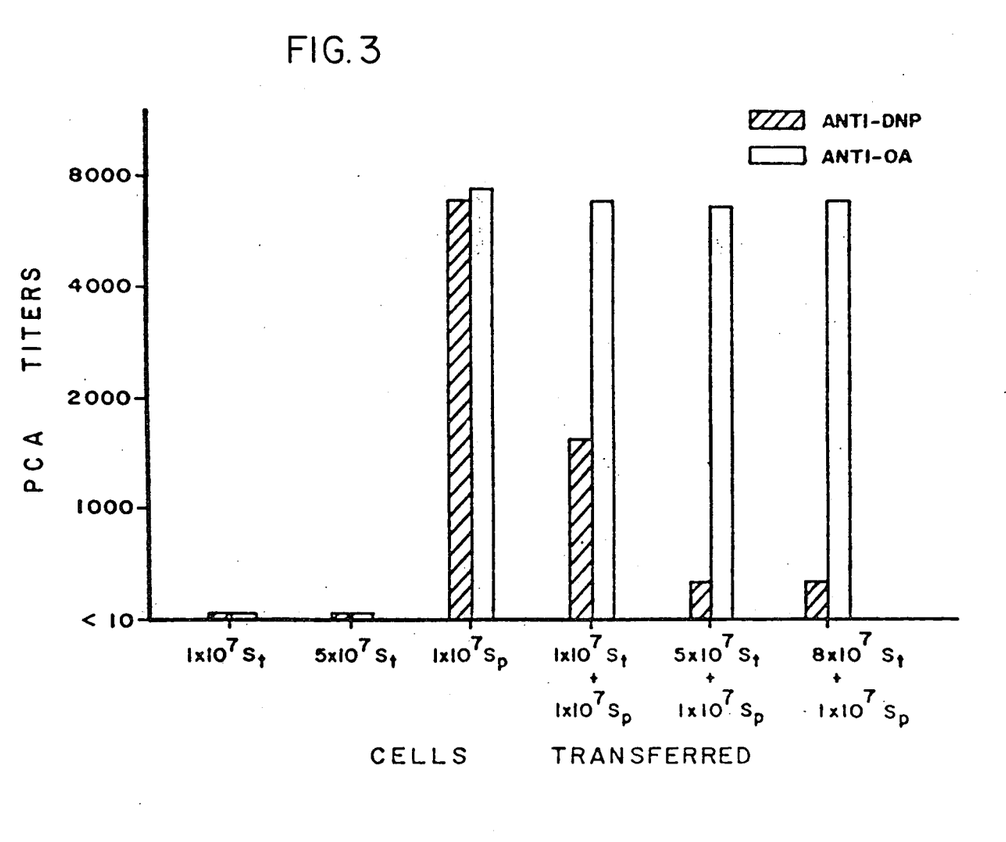
FIG. 3.—Active suppression of anti-DNP IgE response of primed cells with tolerized cells in adoptive transfer system

Different combinations of spleen cells from primed ($S_p$) and tolerized ($S_t$) mice, as indicated in the Fig., were transferred into X-irradiated (650 R) recipients. The primed donors were sensitized with $DNP_3$-OA 30 days before the cell transfer, whereas the tolerized donors received only a single injection of 1 mg $DNP_{2.4}$-$PVA_{10}$ 7 days prior to cell transfer. The IgE responses to both the hapten and the carrier protein, represented by the hatched and open bars, respectively, were measured in terms of PCA titers 14 days after cell transfer.

CONCLUSIONS

From the above, it may be concluded that the PVA conjugates described in the present invention suppress

TABLE X

PREVENTION OF SYSTEMIC ANAPHYLAXIS BY TREATMENT OF SENSITIZED MICE WITH $DNP_{2.4}$—$PVA_{10}$

| GROUP | TREATMENT OF MICE SENSITIZED ON DAY −21* | | PCA TITERS** | | SYSTEMIC REACTION ON CHALLENGE WITH | |
|---|---|---|---|---|---|---|
| | | | ANTI-DNP | ANTI-OA | $DNP_9$—$M_\gamma G$ | OA |
| CONTROL (5 mice) | Day 0: | $DNP_3$—OA + $Al(OH)_3$ + B. pertussis | 3,320 | 3,470 | Death in 41, 44, 44, 47 and 49 min. | Death in 11, 11, 15, 18 and 25 min. |
| | Day 7: | Challenge i.v. with 2 mg $DNP_9$—$M_\gamma G$ or OA | | | | |
| TEST (5 mice) | Day −1: | 1 mg $DNP_{2.4}$—$PVA_{10}$ | <10 | 2,560 | No symptoms (5 mice) | Death in 15, 18, 19, 19 and 21 min. |
| | Day 0: | $DNP_3$—OA + $Al(OH)_3$ + B. pertussis | | | | |
| | Day 7: | Challenge i.v. with 2 mg $DNP_9$—$M_\gamma G$ or OA | | | | |

*All mice received a sensitizing dose of $DNP_3$—OA + $(Al(OH)_3)$ 3 weeks before the experiment. Mice in Group I were resensitized on day 0 with 1 µg of $DNP_3$—OA suspended in 1 mg $Al(OH)_3$ and $8 \times 10^9$ B. pertussis. Mice in Group II received an additional i.p. injection of 1 mg of $DNP_{2.4}$—$PVA_{10}$ one day before resensitization. After 7 days, mice were bled and challenged i.v. with 2 mg of $DNP_9$—$M_\gamma G$ or OA, as indicated in the Table.
**The PCA titers refer to the reaginic antibodies in sera of mice 7 days after immunization.

the formation of IgE antibodies to the appropriate haptens and that the mechanism underlying this suppression may involve the production of suppressor cells, which interfere actively with the corresponding IgE-producing lymphoid cells.

It will be appreciated by those skilled in the art that the treatment of humans with BPO-PVA conjugates prepared as described in the present invention differs significantly from currently available therapeutic procedures in several respects. To begin with, the conjugate will be used in the treatment of humans who already are sensitive to penicillin (and thus the sensitizing step(s) for induction of sensitivity to BPO, which was used in experimental animals, will not be applicable). In view of the fact that injection of polyvalent BPO conjugates into allergic individuals may lead to typical allergic manifestations due to the release of histamine and other vasoactive compounds from their mast cells and basophils, it is visualized that a therapeutic regimen for the immunosuppression of anti-BPO IgE antibodies in man would involve the administration of conjugates of BPO and the simultaneous treatment of the patients with anti-allergic drugs. In this connection, it is interesting to note in Table IV that conjugates with very low epitope density, such as $BPO_{1.1}$-PVA, were still highly effective in suppressing the anti-BPO IgE response. Moreover, it has been recently found that the tolerogenic $BPO_{1.1}$-PVA conjugate elicited only very weak PCA reactions in rats sensitized intradermally with mouse anti-BPO reaginic antibodies. Hence, the possibility of eliciting systemic reactions in allergic patients on treatment with tolerogenic conjugates might be minimized or eliminated by the use of PVA conjugates with low epitope density. In this respect, the BPO-PVA conjugates described in this invention have superior therapeutic values over other tolerogenic conjugates, such as BPO-isologous γ-globulins or BPO-D-GL, which required high epitope density in order to be tolerogenic.

On the basis of the evidence presented for both the DNP and BPO IgE antibody systems, it may also be postulated that this treatment could be extended to the suppression of allergies to other antibiotic molecules by administration of conjugates consisting of PVA coupled to the antilbiotic molecules in question.

The embodiments of the invention in which an exclusive property or privilege is claimed are defined as follows:

1. A process for the preparation of nonimmunogenic conjugates, suitable for suppressing the formation of reaginic antibodies to penicillin (BPO) in a host, the said conjugate being prepared by the reaction of penicillin G in the presence of a suitable salt, at alkaline pH, with an amino derivative of the water-soluble, nonimmunogenic polymer, polyvinyl alcohol (PVA).

2. A process as stated in claim 1, wherein the amino derivative of PVA is prepared by reacting 1,6-hexanediamine with polyvinyl alcohols which had been activated with cyanogen bromide at a pH range of 9-11.

3. A process as stated in claim 1, wherein the polyvinyl alcohol has a molecular weight in the range of 10,000 to 14,000.

4. A process as stated in claim 1, in which the suitable salts are selected from the group consisting of potassium carbonate and sodium carbonate.

5. A process as stated in claim 1, in which the alkaline pH had a range of 8-11.

6. A conjugate consisting of BPO groups coupled to polyvinyl alcohol, suitable for suppressing the formation of reaginic antibodies to penicillin in an allergic host, the conjugate containing an average of 0.7 to 3.9 BPO groups per molecule of polyvinyl alcohol, the said conjugate being prepared according to the process of claim 1.

7. A process according to claim 1 wherein said alkaline pH is 9.8.

* * * * *